US00PP21420P2

(12) United States Plant Patent
Bergman

(10) Patent No.: US PP21,420 P2
(45) Date of Patent: Oct. 26, 2010

(54) ***CHRYSANTHEMUM* PLANT NAMED 'YOAPPLE VALLEY'**

(50) Latin Name: *Chrysanthemum×morifolium*
Varietal Denomination: Yoapple Valley

(75) Inventor: Wendy R. Bergman, Lehigh Acres, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/586,708

(22) Filed: Sep. 25, 2009

(51) Int. Cl.
*A01H 5/00* (2006.01)

(52) U.S. Cl. ..... Plt./286

(58) Field of Classification Search ..... Plt./286
See application file for complete search history.

*Primary Examiner*—Annette H Para
(74) *Attorney, Agent, or Firm*—S. Matthew Edwards

(57) ABSTRACT

A new *Chrysanthemum* plant named 'Yoapple Valley,' particularly distinguished by the single flower form with large red-purple and white bicolored ray florets, uniform habit and flowering response that is early, extremely strong stems, medium green foliage color, and excellent shelf life.

1 Drawing Sheet

Latin name of the genus and species of the plant claimed: *Chrysanthemum×morifolium.*

Varietal denomination: 'Yoapple Valley'.

BACKGROUND OF THE NEW PLANT

The present invention comprises a new *Chrysanthemum*, botanically known as *Chrysanthemum×morifolium*, and hereinafter referred to by the variety name 'Yoapple Valley'.

'Yoapple Valley' is a product of a planned breeding program. The new cultivar has single flower form with large red-purple and white bicolored ray florets, uniform habit and flowering response that is early, extremely strong stems, medium green foliage color, and excellent shelf life.

'Yoapple Valley' originated from a hybridization made in January 2004 in a controlled breeding environment in Salinas, Calif. The female parent was the proprietary, plant designated 'Yolaporte,' U.S. Plant Pat. No. 13,917, with daisy spoon flower form with a little more red-purple color in on the ray florets, and more upright habit.

The male parent of 'Yoapple Valley' is a proprietary, unpatented line identified as 'YB-A2579' with single flowers with purple floret color, with a more vigorous habit, and produces more pollen.

'Yoapple Valley' was selected as one flowering plant within the progeny of the stated cross in December 2006, grown out doors in a field covered by saran in Fort Myers, Fla.

The first act of asexual reproduction of 'Yoapple Valley' was accomplished when vegetative cuttings were propagated from the initial selection in March 2006, in a controlled environment in Fort Myers, Fla.

A Plant Breeder's Right for this cultivar was applied for in Canada in March 2009. 'Yoapple Valley' has not been made publicly available more than one year prior to the filing of this application.

BRIEF SUMMARY OF INVENTION

Horticultural examination of plants grown from cuttings of the plant initiated in March 2007 and continuing thereafter, has demonstrated that the combination of characteristics as herein disclosed for 'Yoapple Valley' are firmly fixed and are retained through successive generations of asexual reproduction.

'Yoapple Valley' has not been observed under all possible environmental conditions.

The phenotype may vary significantly with variations in environment such as temperature, light intensity and day length.

The following traits have been repeatedly observed and are determined to be basic characteristics of the new variety. The combination of these characteristics distinguishes this *Chrysanthemum* as a new and distinct variety

BRIEF DESCRIPTION OF THE PHOTOGRAPHS

The accompanying photographic drawing shows typical flower and foliage characteristics of 'Yoapple Valley' with colors being as true as possible with an illustration of this type.

The photographic drawing shows four flowering potted plants of the new variety growing in a 5 inch pot, and a close-up of the flowers.

DETAILED BOTANICAL DESCRIPTION

The plant descriptions, measurements and aforementioned photographs were taken in Gilroy, Calif. in April 2009 under greenhouse conditions. These plants were started and grown in central coastal California, then shipped to Gilroy, Calif. in April 2009. Plants were grown under conditions which approximate those generally used in commercial potted *Chrysanthemum* production and were about 9 weeks of age.

Color references are made to The Royal Horticultural Society Colour Chart (R.H.S.) 2001.

TABLE 1

DIFFERENCES BETWEEN THE NEW VARIETY 'YOAPPLE VALLEY' AND A SIMILAR VARIETY

| | 'Yoapple Valley' | 'Yospirit Lake' (U.S. Plant Pat. No. 19,207) |
|---|---|---|
| Flower size: | Larger | Smaller |
| Foliage color: | Lighter | Darker |
| Internode length: | Longer | Shorter |
| Stem strength: | Very strong | Moderately strong |

Plant:
*Form, growth and habit.*—Herbaceous pot-type; short and upright, freely branching. Suitable for production- disbudded, center budded or no bud removal.
*Plant height.*—20-25 cm.
*Plant height (inflorescence included).*—25-29 cm.
*Plant width.*—18-20 cm.
Roots:
*Number of days to initiate roots.*—4 days at about 22 degrees C.
*Number of days to produce a rooted cutting.*—10 days at 22 degrees C.
*Type.*—Fine, fibrous, free branching.
*Color.*—RHS N155B but whiter.
Foliage:
*Arrangement.*—Alternate, simple.
*Immature, leaf color, upper surface.*—Closest to RHS 147A.
*Lower surface.*—Closest to RHS 137B.
*Mature, leaf color, upper surface.*—Closest to RHS 137A.
*Lower surface.*—Closest to RHS 137C.
*Length.*—9-9.5 cm.
*Width.*—5.5-6.0 cm.
*Shape.*—Ovate.
*Base shape.*—Accuminate.
*Apex shape.*—Mucronulate.
*Margin.*—Palmately lobed, somewhat serrate.
*Texture, upper surface.*—Bi-fid T-shaped hairs.
*Lower surface.*—Bi-fid T-shaped hairs.
*Color of veins, upper surface.*—RHS 146D.
*Color of veins, lower surface.*—RHS 146D.
*Petiole color.*—RHS 146D.
*Length.*—1.5 cm.
*Diameter.*—0.2-0.3 cm.
*Texture.*—Bi-fid T-shaped hairs.
Stem:
*Quantity of main branches per plant.*—3-4.
*Quantity of leaves per branch.*—8-12.
*Color of stem.*—Closest to RHS 147C.
*Length of stem.*—17-23 cm.
*Diameter.*—0.3-0.4 cm.
*Length of internodes.*—1.0-2.5 cm.
*Texture.*—Bi-fid T-shaped hairs.
*Color of peduncle.*—Closest to RHS 146B, appears lighter because of so many hairs.
*Length of peduncle.*—2.5-3.0 cm.
*Peduncle diameter.*—0.3 cm.
*Texture.*—Bi-fid T-shaped hairs.
Inflorescence:
*Type.*—Composite type, solitary inflorescences (decorative-type) borne terminally above foliage, ray florets arranged acropetally on a capitulum.
*Quantity of short days to flowering (response time).*—50-55 days.
*Quantity of inflorescences per plant.*—4-6.
*Lastingness of individual blooms on the plant.*—55 days.
*Fragrance.*—Slight.
Bud (just before opening/showing color):
*Color.*—RHS 1C, with a hint of RHS 61B.
*Length.*—1-1.5 cm.
*Width.*—1-1.4 cm.
*Shape.*—Oblate.
Immature inflorescence:
*Diameter.*—6.5-7.0 cm.
*Color of ray florets, upper surface.*—RHS 155DC to RHS 155D ground color heavily overlaid with closest to RHS 61B but a more deeper burgundy more heavily in the center, margins, and the apex.
*Lower surface.*—RHS 155A with RHS 60B in slight striations at the apex.
Mature inflorescence:
*Diameter.*—11.5-12.0 cm.
*Total diameter of 'disc'.*—2.5 cm.
Ray florets:
*Average quantity of florets.*—27-31.
*Color of florets, upper surface.*—RHS 155D but a little whiter ground color, overlaid with RHS 70A to RHS 70B slightly striated and more heavily in the center, margins, and more solid color toward the apex.
*Lower surface.*—RHS 155B but whiter, with RHS 70A at the apex.
*Length.*—5.3-5.8 cm.
*Width.*—1.4-1.5 cm.
*Shape.*—Oblong.
*Apex shape.*—Irregularly rounded.
*Margin.*—Entire.
*Texture, upper surface.*—Papillose.
*Lower surface.*—Papillose.
Disc florets:
*Average quantity of florets.*—Approximately 250-300.
*Color of florets.*—RHS 9A.
*Length.*—0.5-0.6 cm.
*Width.*—0.1 cm.
*Shape.*—Tubular, enlongated.
*Apex shape.*—Acute, 5 pointed.
Phyllaries:
*Quantity.*—About 15-20.
*Color, upper surface.*—RHS 137C, with RHS 144B margins which become papery and opaque.
*Lower surface.*—RHS 137C, with RHS 144B margins which become papery and opaque.
*Length.*—0.5-0.6 cm.
*Width.*—0.2-0.25 cm.
*Shape.*—Lanceolate.
*Apex shape.*—Acute.
*Based.*—Fused.
*Margins.*—Entire, which become papery with age.
*Texture, upper surface.*—Glossy and smooth.
*Lower surface.*—Bi-fid T-shaped hairs.
Reproductive organs:
*Pistil.*—1.
*Length.*—0.7 cm.
*Style color.*—RHS N144A.
*Style length.*—0.6 cm.
*Stigma color.*—RHS 9A.
*Stigma shape.*—Bi-parted.
*Ovary color.*—About RHS 155C.
*Stamens.*—4.
*Color of filaments.*—RHS N144A, a little translucent like.
*Length filaments.*—0.3 cm.
*Anther color.*—RHS 9A.
*Anther length.*—0.1 cm.
*Anther shape.*—Oblong.
*Color of pollen.*—RHS 8C.
*Pollen amount.*—Scarce.
*Fertility/seed set.*—Has not been observed on this hybrid.
Disease/pest resistance: Disease resistance or susceptibility has not been observed on this hybrid.

What is claimed is:

1. A new and distinct variety of *Chrysanthemum* plant named 'Yoapple Valley,' substantially as illustrated and described herein.

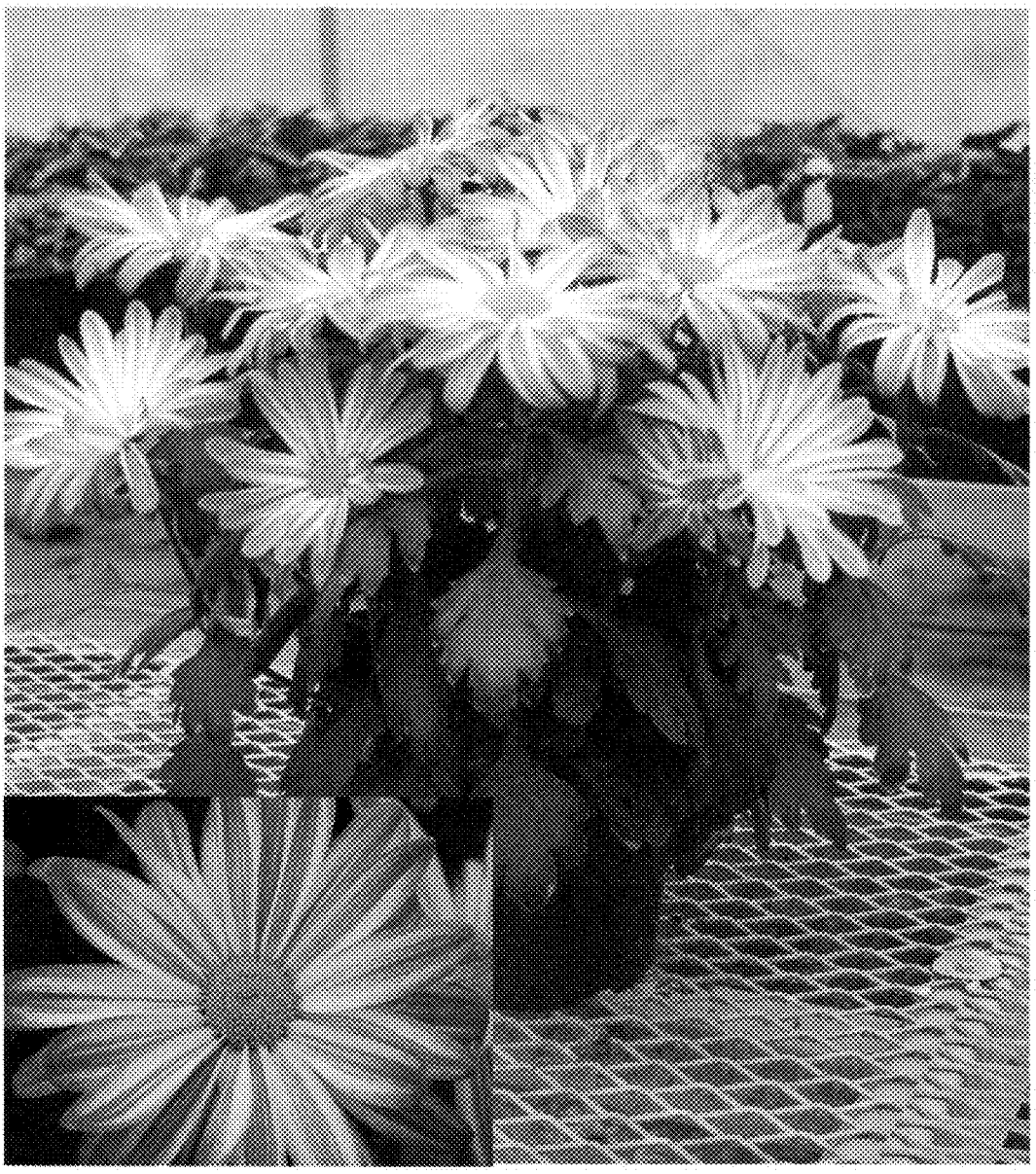

* * * * *